United States Patent [19]

Holmes

[11] Patent Number: 4,959,221

[45] Date of Patent: Sep. 25, 1990

[54] PEST EXTERMINATING COMPOSITION

[76] Inventor: Iris Holmes, 27 Greenbriar, Princeton Community Village, Princeton, N.J. 08540

[21] Appl. No.: 270,139

[22] Filed: Nov. 14, 1988

[51] Int. Cl.$^5$ ............................................. A01N 59/14
[52] U.S. Cl. ....................................... 424/659; 424/84
[58] Field of Search ................. 424/84, 659, 657, 658, 424/660

[56] References Cited

U.S. PATENT DOCUMENTS

| | | | |
|---|---|---|---|
| 360,700 | 4/1887 | Kaatz et al. | 424/658 |
| 490,688 | 1/1893 | Smith | 424/648 |
| 1,029,203 | 6/1912 | Loewenthal | 424/658 |
| 1,204,794 | 11/1916 | Levy | 424/10 |
| 1,636,688 | 7/1927 | Harris | 424/410 |
| 1,893,008 | 1/1933 | Wamoscher | 44/7.6 |
| 2,015,062 | 9/1935 | Benjamin | 23/293 R |
| 2,088,651 | 8/1937 | Henninger | 424/627 |
| 4,363,798 | 12/1982 | D'Orazio | 424/84 |
| 4,369,176 | 1/1983 | Ott | 424/84 |
| 4,438,090 | 3/1984 | Brite | 424/10 |
| 4,461,758 | 7/1984 | Brite | 424/10 |
| 4,617,188 | 10/1986 | Page et al. | 514/780 |

FOREIGN PATENT DOCUMENTS 58-52205 3/1983 Japan .
AD 1896 of 1896 United Kingdom .

Primary Examiner—Allen J. Robinson
Attorney, Agent, or Firm—Sperry, Zoda & Kane

[57] ABSTRACT

A pest exterminating composition which is particularly usable for controlling of roaches and mice which includes in combination boric acid, sugar and coconut. Preferably the boric acid comprises approximately one-half of the composition with the sugar preferably in a powdered form comprising 37.5% of the composition. The coconut is preferably shredded and raw and comprises approximately 12.5% of the composition. The mixture provides a pesticide which is attractive to the animals and is in powder form such as to provide a substantial lifetime in position awaiting consumption by the mice or roaches in the area.

7 Claims, No Drawings

PEST EXTERMINATING COMPOSITION

BACKGROUND OF THE INVENTION
1. Field Of The Invention

The present invention deals with the field of devices for exterminating pests such as roaches and mice. Some extermination systems include traps or means of retaining the pests. Other devices include the concept of providing an ingestible poison.

The present invention deals with the field of products of compositions which have ingestible poisons which are attractive by being tasty for a variety of different types of pests such as mice, roaches and other insects.

2. Description Of The Prior Art

Various products have been utilized for controlling of mice, roaches and other insects such as U.S. Pat. No. 360,700 patented Apr. 5, 1887 to I. Kaatz et al on an Insecticide; U.S. Pat. No. 490,688 patented Jan. 31, 1893 to D. Smith on an Insecticide; U.S. Pat. No. 1,029,203 patented June 11, 1912 to O. Loewenthal on an Insectifuge; U.S. Pat. No. 1,204,794 patented Nov. 14, 1916 to L. Levy on a Poison-Deterrent; U.S. Pat. No. 1,636,688 patented July 26, 1927 to P. Harris on a Composition And Method Of Preparing Roach Tablets; U.S. Pat. No. 1,893,008 patented Jan. 3, 1933 to L. Wamoscher on a Method And Means For Prevention Of Metaldehyde Poisonings; U.S. Pat. No. 2,015,062 patented Sept. 24, 1935 to C. Benjamin on a Method For Producing Colored Salts; U.S. Pat. No. 2,088,651 patented Aug. 3, 1937 A. Henninger on an Insecticide; U.S. Pat. No. 4,363,798 patented Dec. 14, 1982 to V. D'Orazio on a Termite Bait Composition; U.S. Pat. No. 4,369,176 patented Jan. 18, 1983 to J. Ott on a Method Of Attracting And Killing Insects; U.S. Pat. No. 4,438,090 patented March 20, 1984 to A. Brite on a Method Of Preparing An Insecticide Containing Boric Acid; U.S. Pat. No. 4,461,758 patented July 24, 1984 to A. Brite on an Insecticide Including Powdered Boric Acid; and U.S. Pat. No. 4,617,188 patented Oct. 14, 1986 to E. Page et al on Natural Insecticides Employing Borax And Carob.

SUMMARY OF THE INVENTION

The present invention provides a pest extermination composition which is particularly usable for controlling of insects such as roaches as well as larger animal pests such as mice. Boric acid preferably in a dry powdered form comprises approximately 50% of the total composition by weight. A powdered sugar component is added thereto of a ratio of approximately 37.5% by weight. Finally dried and shredded coconut is added to a weight percentage of approximately 12.5%. The boric acid is the killing component whereas the powdered sugar is attractive to certain types of pests. The dried and shredded coconut is tasty for other types of pests. Also the mixture of the dried coconut and the powdered sugar and powdered boric acid when mixed provides an overall final dried composition which lasts for an extended period of time in place under kitchen counters or behind kitchen appliances and so forth and thereby does not have to be replaced periodically as with other non-dry poisons designed to be ingested by pests.

The coconut component is preferably shredded and can be roasted to remove any moisture and at least a portion of the coconut oil therein. In this manner the final raw coconut is found to be quite tasty by animals such as mice. The sugar which is also powdered and therefore is dried provides the means for attracting other types of animals and most insects such as roaches.

It is an object of the present invention to provide a pest exterminating composition particularly usable for controlling of roaches and mice wherein all components are dried or of powder consistency such that when mixed the final product can be placed for extended periods of time in those areas frequently visited by the pests.

It is an object of the present invention to provide a pest exterminating composition particularly usable for controlling of roaches and mice wherein cost of components is minimized.

It is an object of the present invention to provide a pest exterminating composition particularly usable for controlling of roaches and mice wherein a broad spectrum of different types of pests such as mice, roaches and other insects can be attracted to the same poison.

It is an object of the present invention to provide a pest exterminating composition particularly usable for controlling of roaches and mice wherein poisoning by ingestion is made possible for a great variety of different types of pests.

It is an object of the present invention to provide a pest exterminating composition particularly usable for controlling of roaches and mice wherein boric acid, sugar and coconut are mixed in dried or powdered form in the readily available off-the-shelf configurations.

It is an object of the present invention to provide a pest exterminating composition particularly usable for controlling of roaches and mice wherein shredded coconut is dried and roasted to maintain the mixture with powdered sugar and powdered boric acid in a self-adhering consistency.

It is an object of the present invention to provide a pest exterminating composition particularly usable for controlling of roaches and mice wherein powdered sugar is included in the composition but is prevented from hardening by the mixture thereof with shredded coconut.

It is an object of the present invention to provide a pest exterminating composition particularly usable for controlling of roaches and mice wherein 100% raw coconut can be mixed with powdered sugar and powdered boric acid to provide a final composition ingested by a wide variety of different types of pests.

DETAILED DESCRIPTION OF THE PREFERRED EMBODIMENT

The preferred embodiment of the present invention includes powdered boric acid of approximately 50% by weight in combination with powdered sugar of approximately 37.5% by weight. The final component is preferably dried and shredded coconut approximately 12.5% by weight.

The powdered sugar preferably can take the form of conventional powdered sugar available such as in cake icing mixes and the like but actually any type of powdered sugar can be usable. The boric acid is commonly available in powder consistency which is completely dry which is necessary in order to extend the amount of time that the final composition can be maintained in a single location without replacement thereof.

The coconut which comprises approximately one-eighth of the total weight of the final mixture is preferably dried to remove water and some coconut oil therefrom and can be roasted for this purpose. The coconut also is preferably shredded to facilitate mixing with the sugar and boric acid which are both in a powdered format.

The consistency of the composition will be a dried powder which can be easily placed in small containers being open on the top to facilitate ingestion thereof by pests such as mice or roaches and other insects.

The inclusion of both powdered sugar and shredded coconut greatly enhances the final product. In particular powdered sugar itself draws a great number of insects such as roaches or other insect pests which are desired to be exterminated. The coconut is also extremely tasty and tends to encourage ingestion of the poison by larger pests such as mice. This combination provides a broad spectrum of possible pests which can ingest the same identical poison and as such provide full and complete control of pests within a kitchen or other similar environment.

Powdered sugar also has a tendency to absorb moisture and subsequently hardened. The mixture of the powdered sugar with the coconut minimizes this moisture absorption due to the residual oil which always remains within the coconut which tends to keep moisture out of the final composition of matter.

The proportions which are found to be most ideal for attracting a broad spectrum of different pests has been shown to be one-half boric acid in combination with three-eighths powdered sugar and one-eighth coconut with measurements being taken by weight. However other compositions slightly varying in percentage from this particular composition have also been shown to be effective and come within the concept and claims of the present invention.

While particular compositions of this invention have been described above, it will be apparent, that many changes may be made in the form and arrangement of the various elements of the combination. In consideration thereof it should be understood that preferred compositions of this invention disclosed herein are intended to be illustrative only and not intended to limit the scope of the invention.

I claim:

1. A pest exterminating composition particularly usable for controlling of roaches and mice which comprises:
   (a) powdered boric acid of from 1% to 75% by weight;
   (b) powdered sugar of from 1% to 75% by weight; and
   (c) a dried shredded coconut component of from 1% to 50% by weight, said coconut component being dried to remove oils therefrom.

2. A pest exterminating composition particularly usable for controlling of roaches and mice as defined in claim 1 comprising 45% to 55% by weight of boric acid component.

3. A pest exterminating composition particularly usable for controlling of roaches and mice as defined in claim 1 comprising 35% to 40% by weight of sugar component.

4. A pest exterminating composition particularly usable for controlling of roaches and mice as defined in claim 1 comprising 10% to 15% by weight of coconut component.

5. A pest exterminating composition particularly usable for controlling of roaches and mice as defined in claim 1 comprising approximately 50% by weight of boric acid component.

6. A pest exterminating composition particularly usable for controlling of roaches and mice as defined in claim 1 comprising approximately 37.5% by weight of sugar component.

7. A pest exterminating composition particularly usable for controlling of roaches and mice as defined in claim 1 comprising 12.5% by weight of coconut component.

* * * * *